(12) United States Patent
Mata et al.

(10) Patent No.: US 12,564,411 B2
(45) Date of Patent: Mar. 3, 2026

(54) FRICTION COMPENSATING, EVEN PRESSURE CLIP

(71) Applicant: AtriCure, Inc., Mason, OH (US)

(72) Inventors: Carol Ann Mata, Cincinnati, OH (US); Frank M. Fago, Mason, OH (US)

(73) Assignee: AtriCure, Inc., Mason, OH (US)

( * ) Notice: Subject to any disclaimer, the term of this patent is extended or adjusted under 35 U.S.C. 154(b) by 295 days.

(21) Appl. No.: 18/483,192

(22) Filed: Oct. 9, 2023

(65) Prior Publication Data

US 2024/0138847 A1 May 2, 2024

Related U.S. Application Data

(60) Provisional application No. 63/380,971, filed on Oct. 26, 2022.

(51) Int. Cl.
*A61B 17/128* (2006.01)

(52) U.S. Cl.
CPC .................................. *A61B 17/1285* (2013.01)

(58) Field of Classification Search
CPC . A61B 17/122; A61B 17/1227; A61B 17/128; A61B 17/1285; A61B 2017/00584; A61B 2017/00588
See application file for complete search history.

(56) References Cited

U.S. PATENT DOCUMENTS

| | | | |
|---|---|---|---|
| 6,428,548 B1 | 8/2002 | Durgin et al. | |
| 7,862,571 B2 | 1/2011 | Dennis | |

| | | | |
|---|---|---|---|
| 8,852,218 B2 | 10/2014 | Hughett, Sr. et al. | |
| 9,883,863 B2 | 2/2018 | Hughett, Sr. et al. | |
| 9,936,953 B2 * | 4/2018 | Thompson | A61B 17/3468 |
| 10,098,640 B2 * | 10/2018 | Bertolero | A61B 17/083 |
| 10,231,734 B2 * | 3/2019 | Thompson | A61F 5/0089 |
| 10,278,707 B2 * | 5/2019 | Thompson | A61B 17/12009 |
| 11,471,161 B2 | 10/2022 | Hughett, Sr. et al. | |
| 11,998,211 B2 * | 6/2024 | Winkler | A61B 17/1227 |
| 11,998,212 B2 * | 6/2024 | Winkler | A61B 17/12099 |
| 2002/0183768 A1 | 12/2002 | Deem et al. | |
| 2005/0149068 A1 | 7/2005 | Williams et al. | |

(Continued)

FOREIGN PATENT DOCUMENTS

| | | |
|---|---|---|
| WO | 2007/009099 | 1/2007 |
| WO | 2010/011661 | 1/2010 |

*Primary Examiner* — Ryan J. Severson
(74) *Attorney, Agent, or Firm* — Dorton & Willis LLP; Ryan Willis

(57) ABSTRACT

A clip applier and method provide for surgically minimizing or eliminating a tissue appendage of the patient using an occlusion clip. An end effector of the clip applier has first and second channels that respectively receive/engage first and second elongate beams of the clip. The clip includes strand(s) that forms a loop through the first and the second elongate beams. Terminal segments of the strand(s) extend proximally through a clip setting mechanism of the occlusion clip. An opening between first and second elongate beams of the occlusion clip are positioned around a tissue appendage. A closure mechanism of the clip applier is actuated to proximally draw the terminal segments of the strand(s) to close the occlusion clip and to close the end effector. A release mechanism of the occlusion clip is actuated, allowing the end effector to open away from the occlusion clip in a clamped state.

16 Claims, 5 Drawing Sheets

(56)    References Cited

U.S. PATENT DOCUMENTS

| | | | |
|---|---|---|---|
| 2005/0149069 A1* | 7/2005 | Bertolero ................. | A61B 1/12 |
| | | | 606/151 |
| 2005/0277959 A1 | 12/2005 | Cosgrove | |
| 2006/0020271 A1 | 1/2006 | Stewart et al. | |
| 2007/0213747 A1 | 9/2007 | Monassevitch et al. | |
| 2008/0033457 A1 | 2/2008 | Franscischelli et al. | |
| 2008/0039879 A1 | 2/2008 | Chin et al. | |
| 2009/0012545 A1 | 1/2009 | Williamson et al. | |
| 2009/0209986 A1 | 8/2009 | Stewart et al. | |
| 2009/0240266 A1 | 9/2009 | Dennis | |
| 2010/0114124 A1 | 5/2010 | Kelleher et al. | |
| 2011/0009853 A1* | 1/2011 | Bertolero ............. | A61B 17/083 |
| | | | 606/14 |
| 2016/0324527 A1* | 11/2016 | Thompson ....... | A61B 17/00234 |
| 2018/0310936 A9* | 11/2018 | Bertolero ............. | A61B 17/083 |
| 2023/0338032 A1* | 10/2023 | Winkler ............. | A61B 17/1227 |
| 2023/0338033 A1* | 10/2023 | Winkler ........... | A61B 17/12099 |
| 2024/0000458 A1* | 1/2024 | Schneeberger .. | A61B 17/12122 |
| 2024/0138847 A1* | 5/2024 | Mata .................. | A61B 17/1227 |
| 2024/0415518 A1* | 12/2024 | Williamson, IV ... | A61B 17/083 |
| 2025/0082331 A1* | 3/2025 | Fago .................. | A61B 17/1227 |
| 2025/0082339 A1* | 3/2025 | Fago .................. | A61B 17/1227 |

* cited by examiner

FRICTION COMPENSATING, EVEN PRESSURE CLIP

CROSS-REFERENCE TO RELATED APPLICATIONS

The present application claims the benefit of U.S. Provisional Patent Application Ser. No. 63/380,971 filed 26 Oct. 2022 and entitled "Friction Compensating, Even Pressure Clip," the disclosure of which is hereby incorporated by reference in its entirety.

FIELD OF THE INVENTION

The present disclosure is directed to implantable medical devices, and, more specifically, to implantable exclusion devices for anatomical structures, and related instruments and related methods.

BACKGROUND OF THE INVENTION

The present disclosure contemplates that atrial fibrillation is a common heart arrhythmia, affecting millions of people in the United States. In some patients with atrial fibrillation, stagnant blood in the heart's left atrial appendage ("LAA") may be a source of blood clots, which may enter the blood circulation and increase the risk of stroke. Excluding the LAA, which may create electrical and/or fluidic isolation of the LAA, may be beneficial in terms of reducing the atrial fibrillation burden and/or reducing the risk of stroke for some patients. Accordingly, in some patients, it may be desirable to exclude the LAA by securely sealing the LAA orifice at the base of the LAA using an occlusion device.

The present disclosure contemplates that generally known LAA clips are surgically attached to a heart patient concomitant with other open chest surgical procedures such as heart bypass operations. These generally known LAA clips may include springs that hold a pair of beams on each side of the LAA. Spring loaded clips typically require the applier mechanism to be able to withstand the closure force of the clip when the applier mechanism is opening the clip or holding the clip open. Those forces can be up to about 10 pounds, which typically requires an applier having substantial structure. This may limit the ability to minimize the end effector size of the applier mechanism. Thus, these applier mechanisms are typically relatively large.

SUMMARY OF THE INVENTION

According to one aspect of the present disclosure, an apparatus such as an occlusion clip is provided for eliminating or mitigating a tissue appendage of a patient. An example occlusion clip includes a first elongate beam comprising a first bore open at first distal end and a first proximal end. the apparatus comprises a second elongate beam comprising a second bore open at second distal end and a second proximal end. The occlusion clip comprises an elongate strand that is positioned through the first bore and the second bore extending proximally at respective first and second terminal segments from the first and the second proximal ends of the first and the second elongate beams. The occlusion clip comprises a clip setting mechanism that encompasses the first terminal segment and the second terminal segment of the elongate strand. The clip setting mechanism is proximate to the first and the second proximal ends of the first and the second elongate beams. The clip setting mechanism is configured to: (i) allow cinching of the elongate strand to reduce a size of the single strand loop, bringing closer together the first and the second elongate beams; and (ii) retain the single strand loop in a cinched position.

In a detailed embodiment, the clip setting mechanism may include a crimping sleeve. In a detailed embodiment, the clip setting mechanism may include a one-way knot, such as a Meltzer knot.

According to another aspect of the present disclosure, an apparatus such as an occlusion clip is provided for eliminating or mitigating a tissue appendage of a patient. An example occlusion clip comprises a first elongate beam having a first bore open at first distal end and a first proximal end. The occlusion clip comprises a second elongate beam having a second bore open at second distal end and a second proximal end. First and second elongate strands combine to form a loop and distally overlap. The first elongate strand has a first distal terminal segment coupled to the second distal end of the second elongate beam and extending through the first bore of the first elongate beam from the first distal end to extend a first proximal segment proximally from the first proximal end. The second elongate strand has a second distal terminal segment coupled to the first distal end of the first elongate beam and extending through the second bore of the second elongate beam from the second distal end to extend a second proximal terminal segment proximally from the second proximal end. The occlusion clip comprises a clip setting mechanism that encompasses the first and the second terminal segments respectively of the first and the second elongate strands. The clip setting mechanism is proximate to the first and the second proximal ends of the first and the second elongate beams. The clip setting mechanism is configured to: (i) allow cinching of the elongate strand to reduce a size of the single strand loop, bringing together the first and the second elongate beams; and (ii) retain the single strand loop in a cinched position.

In a detailed embodiment, the clip setting mechanism may include a crimping sleeve. In a detailed embodiment, the clip setting mechanism may include a one-way knot, such as a Meltzer knot.

According to an additional aspect of the present disclosure, a clip dispensing device is provided for positioning an occlusion clip for eliminating or mitigating a tissue appendage of a patient. An example clip dispensing device has an end effector comprising: (i) a first channel that receives and engages a first elongate beam of an occlusion clip; and (ii) a second channel that receives and engages a second elongate beam of the occlusion clip, the occlusion clip comprising at least one strand that forms a loop through the first and the second elongate beams and extends terminal segments proximally through a clip setting mechanism. The clip dispensing device has a closure mechanism operative to proximally draw the terminal segments of the at least one strand to close the occlusion clip. The clip dispensing device has a release mechanism that actuates to release the end effector from the occlusion clip, allowing the end effector to open away from the occlusion clip in a clamped state.

In a detailed embodiment, the clip setting mechanism of the occlusion clip may include a crimping sleeve, the clip dispensing device including a crimping tool positioned to contact the crimping sleeve and configured for actuation to crimp the crimping sleeve. In a detailed embodiment, the release mechanism may include a strand cutter operative to sever the at least one strand proximal to the clip setting mechanism.

According to a further aspect of the present disclosure, a method is provided for surgically closing and dispensing an occlusion clip on a tissue appendage of a patient using a clip applier for minimizing or eliminating the tissue appendage. An example method includes surgically inserting an end effector of a clip applier into a body cavity of a patent. The end effector comprises: (i) a first channel that receives and engages a first elongate beam of an occlusion clip; and (ii) a second channel that receives and engages a second elongate beam of the occlusion clip. The occlusion clip comprises at least one strand that forms a loop through the first and the second elongate beams and extends terminal segments proximally through a clip setting mechanism. The method includes positioning an opening between the first and the second elongate beams of the occlusion clip around a tissue appendage of the patient. The method includes actuating a closure mechanism that proximally draws the terminal segments of the at least one strand to close the occlusion clip and close the first and the second channel of the end effector. The method includes actuating a release mechanism that actuates to release the end effector from the occlusion clip, allowing the end effector to open away from the occlusion clip in a clamped state.

In a detailed embodiment, the at least one elongate strand may be positioned through the first bore and the second bore extending proximally at respective first and second terminal segments from the first and the second proximal ends of the first and the second elongate beams.

In a detailed embodiment, the at least one elongate strand may include first and second elongate strands the combine to form a loop and that distally overlap. The first elongate strand may have a first distal terminal segment coupled to the second distal end of the second elongate beam and extending through the first bore of the first elongate beam from the first distal end to extend a first proximal segment proximally from the first proximal end. The second elongate strand may have a second distal terminal segment coupled to the first distal end of the first elongate beam and extending through the second bore of the second elongate beam from the second distal end to extend a second proximal terminal segment proximally from the second proximal end.

In a detailed embodiment, the clip setting mechanism of the occlusion clip may include a crimping sleeve, and the method may include actuating a crimping tool of the clip applier to crimp the crimping sleeve. In a detailed embodiment, actuating the release mechanism may include actuating a strand cutter that severs the at least one strand proximal to the clip setting mechanism.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

Figure 1A:
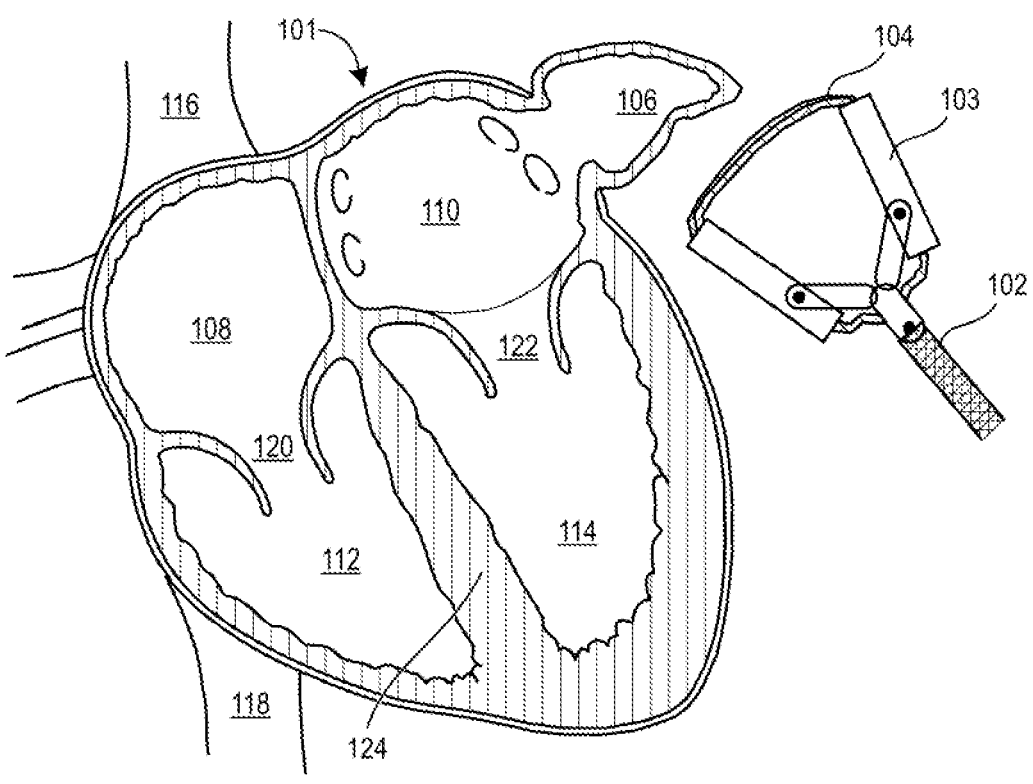
FIG. 1A is a cross section view of a human heart that is being approach by a clip applier having an end effector in an open position that holds a clip for treatment of a left atrial
Figure 1B:
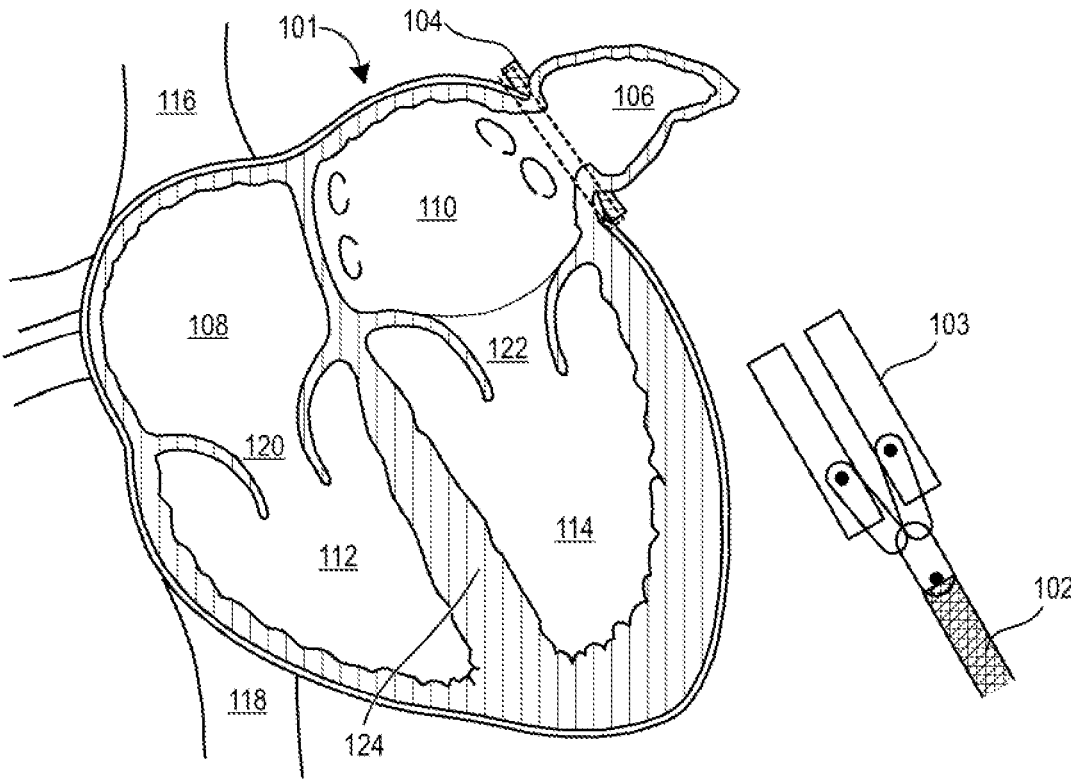
Figure 2A:
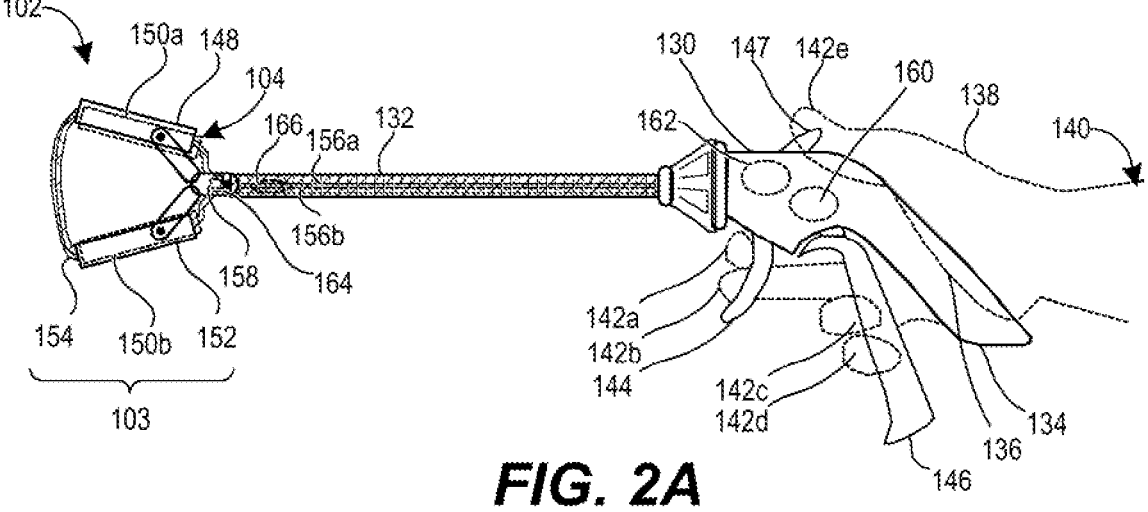
Figure 2B:
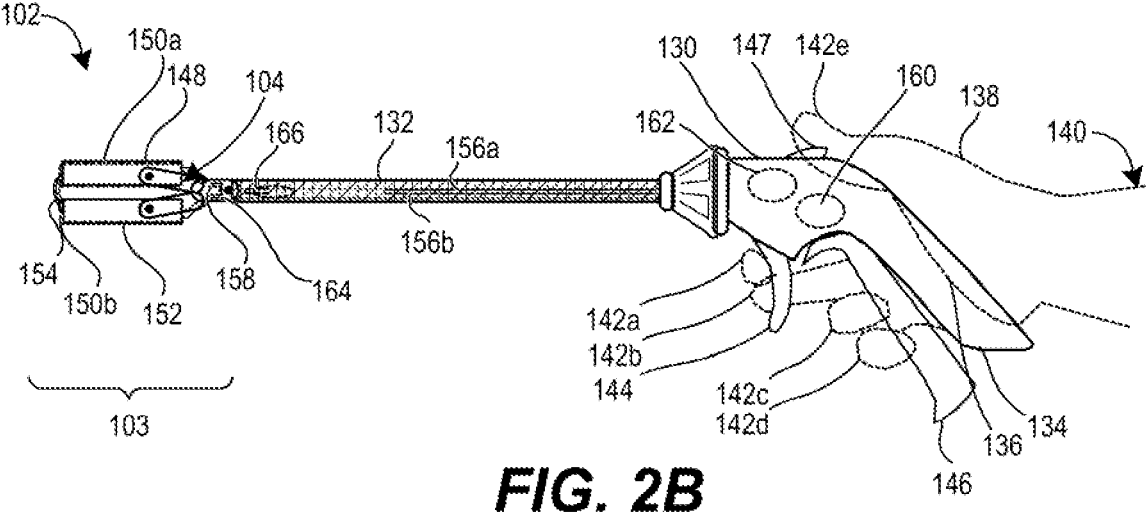
Figure 3A:
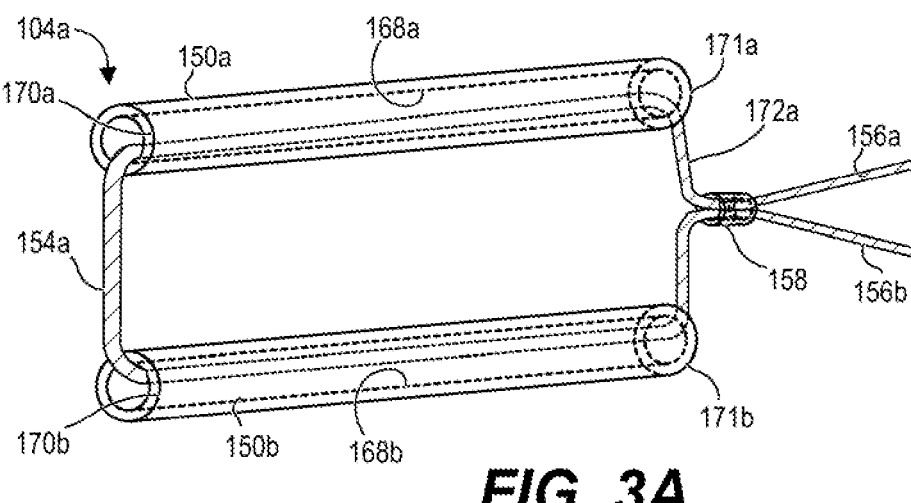
Figure 3B:
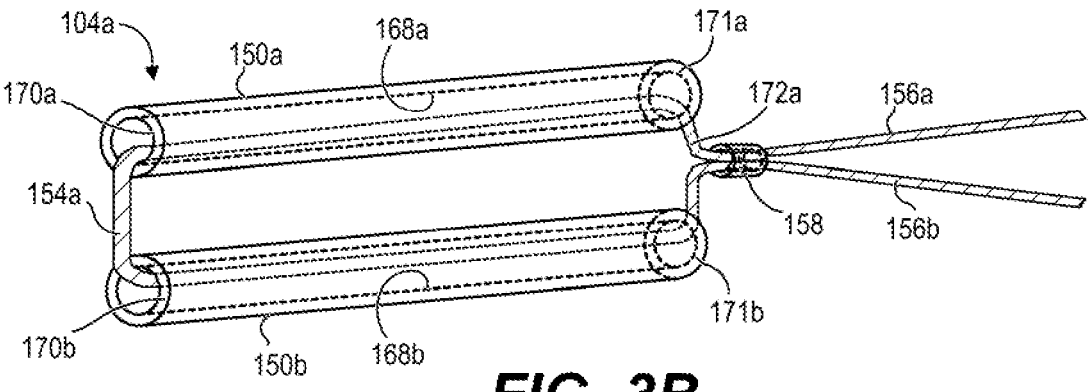
Figure 4:
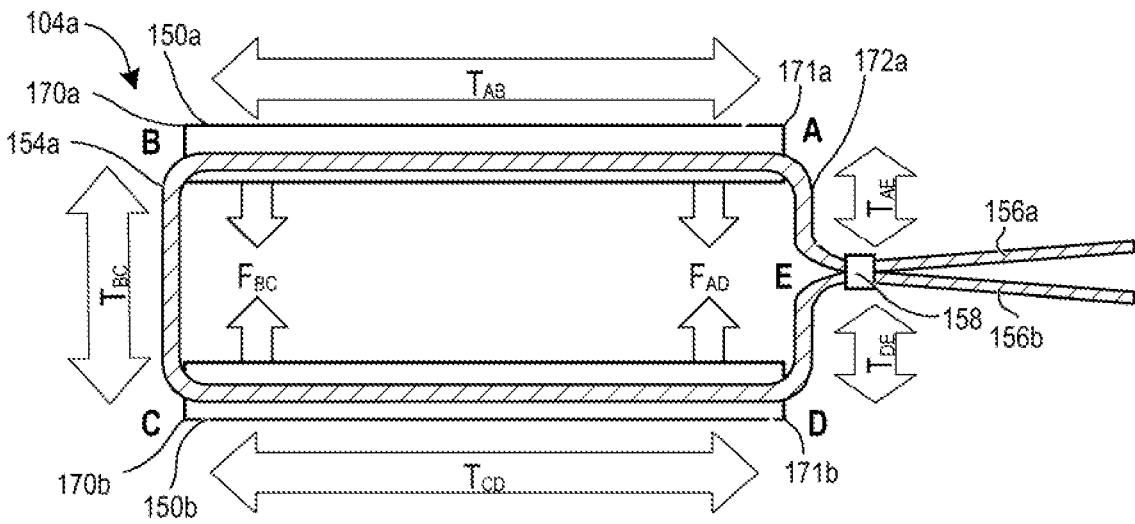
Figure 5A:
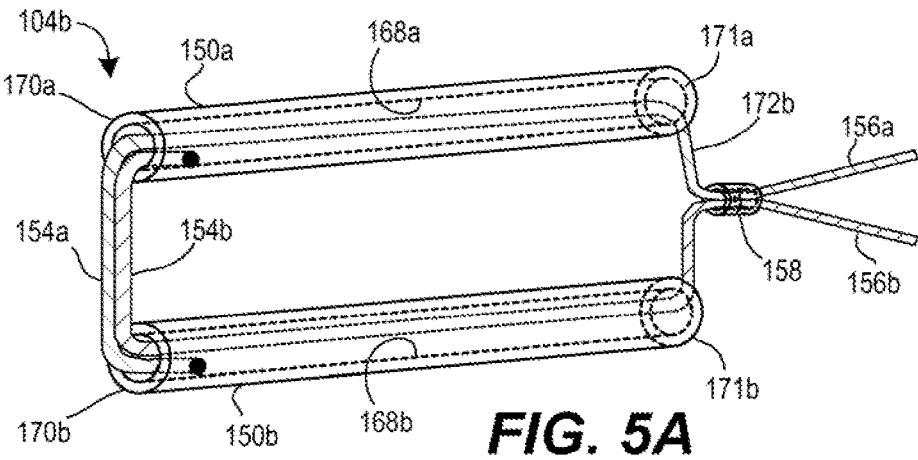
Figure 5B:
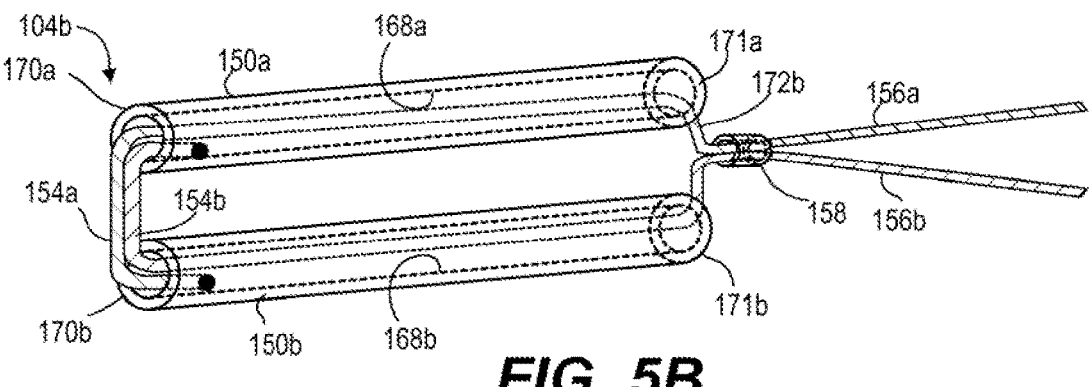
Figure 6:
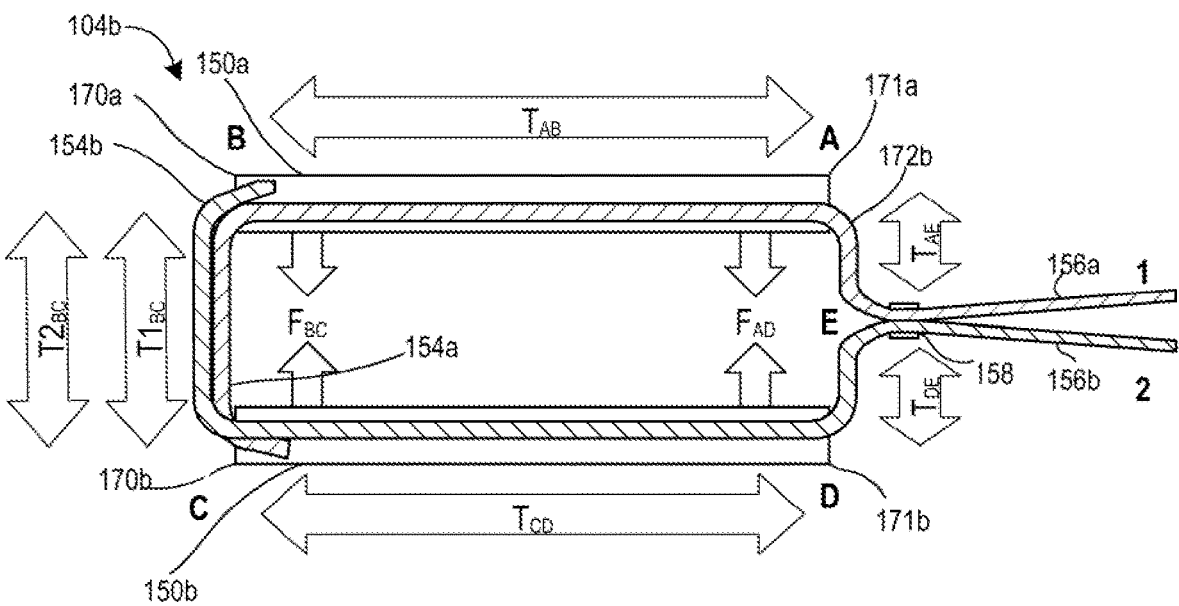
Figure 7:
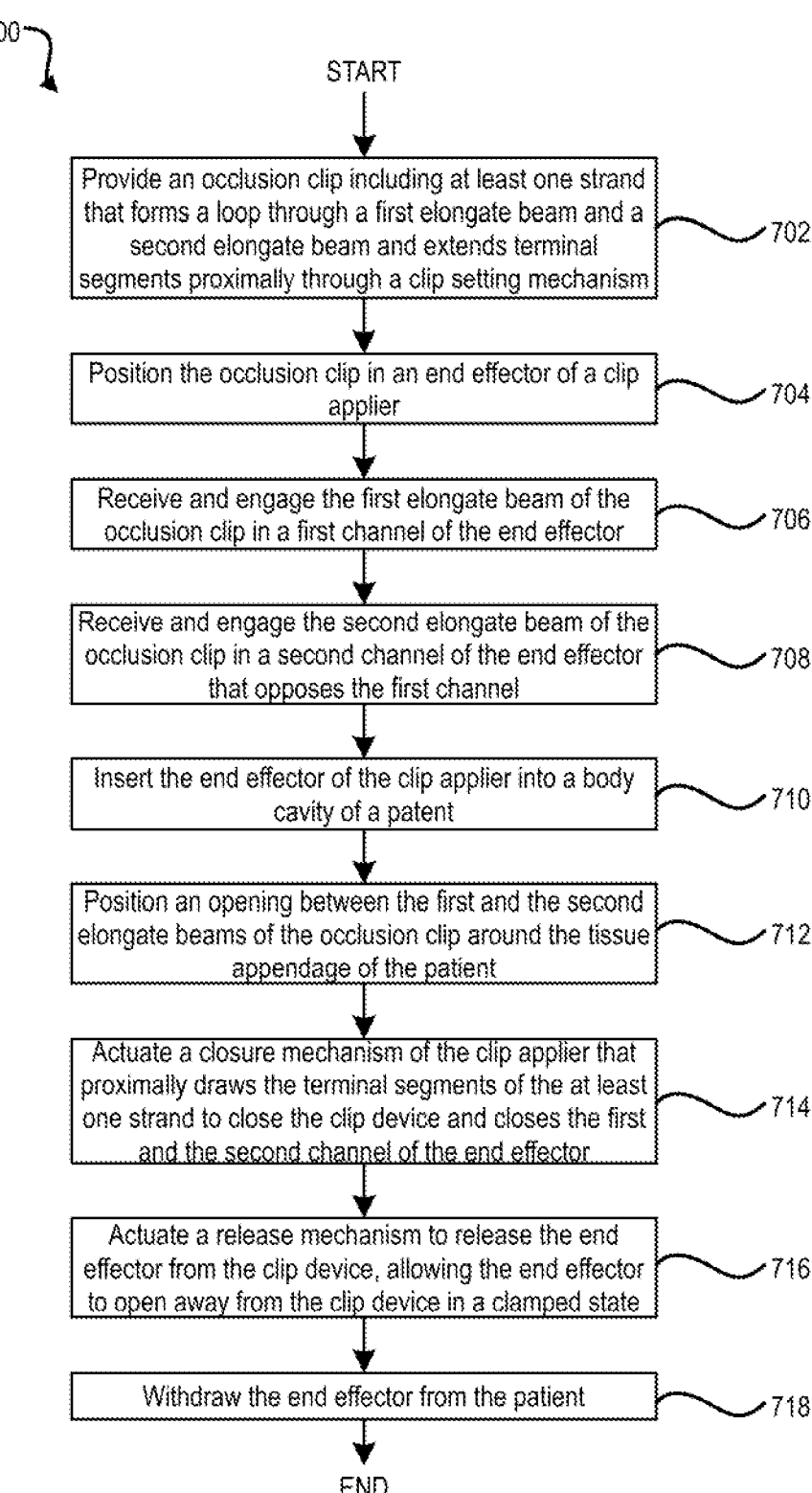

4 appendage (LAA) to prevent certain types of stroke, according to one or more embodiments;

FIG. 1B is a cross section of the human heart after dispensing of the clip by the clip applier, according to one or more embodiments;

FIG. 2A is a side view of the clip applier having the end effector in an open position as actuated by a handle, according to one or more embodiments;

FIG. 2B is a side view of the clip applier having the end effector in a closed position as actuated by the handle, according to one or more embodiments;

FIG. 3A is a three-dimensional view of a single-loop clip that is in an open position, according to one or more embodiments;

FIG. 3B is a three-dimensional view of the single-loop clip that is in a closed position, according to one or more embodiments;

FIG. 4 is a side view of the single-loop clip annotated with forces and tension arrows when closed around an object, according to one or more embodiments;

FIG. 5A is a three-dimensional view of a dual-loop clip that is in an open position, according to one or more embodiments;

FIG. 5B is a three-dimensional view of the dual-loop clip that is in a closed position, according to one or more embodiments;

FIG. 6 is a side view of the dual-loop clip annotated with forces and tension arrows when closed around an object, according to one or more embodiments; and FIG. 7 is a flow diagram presenting a method for surgically closing and dispensing an occlusion clip on a tissue appendage of a patient using clip applier for minimizing or eliminating the tissue appendage, according to one or more embodiments.

DETAILED DESCRIPTION

According to aspects of the present disclosure, a low-profile clip and applier mechanism may provide generally even force on distal and proximal ends of an occlusion clip by using a clip closure mechanism that compensates for friction. As the benefits for Left Atrial Appendage (LAA) exclusion become better known by potential patients, it is conceivable that these patients may want the procedure done as a standalone rather than concomitantly with other cardiac procedures. A barrier to a standalone procedure from a patient perspective is pain and recovery time. A smaller access port greatly facilitates reduced pain and resulting recovery time. Generally known applier mechanisms intended to dispense spring closed clips typically require too large of a structure to be used in a minimally invasive procedure.

The patient also demands a clip that effectively excludes the LAA. The present disclosure contemplates that occlusion clips that apply generally linear, generally even pressure may be extremely effective to exclude the LAA. The present disclosure provides a clip mechanism specifically designed to provide generally even pressure along a pair of opposing beams while being configured to fit through a small opening of about 5 mm or less.

Minimizing the access port in the patient is important to reduce pain and recovery time. A small clip with beams that can be operated in-line can significantly reduce the port size requirements. As discussed below, a simple suture loop with two rigid beams may not provide even pressure due to friction losses at the joints, therefore the distal end may have substantially less closure force than the proximal end. The present disclosure provides a clip that inherently provides more force at the distal end to compensate for friction losses in order to provide generally even pressure along the beams. This clip has no residual forces until the clip is cinched on the LAA, which facilitates the use of small-sized end-effectors and applier mechanisms. Force to open the clip may be minimal (e.g., less than about 1.0 lbs) while providing a locking force of greater than about 5.0 lbs.

In the following detailed description of exemplary embodiments of the disclosure, specific exemplary embodiments in which the various aspects of the disclosure may be practiced are described in sufficient detail to enable those skilled in the art to practice the invention, and it is to be understood that other embodiments may be utilized and that logical, architectural, programmatic, mechanical, electrical, and other changes may be made without departing from the spirit or scope of the present disclosure. The following detailed description is, therefore, not to be taken in a limiting sense, and the scope of the present disclosure is defined by the appended claims and equivalents thereof. Within the descriptions of the different views of the figures, similar elements may be provided with similar names and reference numerals as those of the previous figure(s). The specific numerals assigned to the elements are provided solely to aid in the description and are not meant to imply any limitations (structural or functional or otherwise) on the described embodiment. It will be appreciated that for simplicity and clarity of illustration, elements illustrated in the figures have not necessarily been drawn to scale. For example, the dimensions of some of the elements may be exaggerated relative to other elements.

It is understood that the use of specific component, device and/or parameter names, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that term is utilized.

As further described below, implementation of the functional features of the disclosure described herein may be provided within processing devices and/or structures and can involve use of a combination of hardware, firmware, as well as several software-level constructs (e.g., program code and/or program instructions and/or pseudo-code) that execute to provide a specific utility for the device or a specific functional logic. The presented figures may illustrate both hardware components and software and/or logic components.

Those of ordinary skill in the art will appreciate that the hardware components and basic configurations depicted in the figures may vary. The illustrative components are not intended to be exhaustive, but rather are representative to highlight example components that are utilized to implement aspects of the described embodiments. For example, other devices/components may be used in addition to or in place of the hardware and/or firmware depicted. The depicted examples are not meant to imply architectural or other limitations with respect to the presently described embodiments and/or the general invention. The description of the illustrative embodiments can be read in conjunction with the accompanying figures. Embodiments incorporating teachings of the present disclosure are shown and described with respect to the figures presented herein.

FIG. 1A is a cross section view of a human heart 101 that is being approached by an example applier mechanism or clip applier 102 having an end effector 103 in an open position that holds a clip 104 for treatment of a left atrial appendage (LAA) 106 to prevent certain types of stroke. The human heart 101 has four chambers: (i) right atrium (RA) 108; (ii) left atrium (LA) 110; (iii) right ventricle (RV) 112; and left ventricle (LV) 114. The RA 108 receives blood from the venous vasculature. Venous blood enters the RA 108 from the superior vena cava (SVC) blood vessel 116 and the inferior vena cava (IVC) blood vessel 118. Normal pumping of the heart 101 causes blood in the RA 108 to flow through the tricuspid valve (TV) 120 into the right ventricle (RV) 112. Blood in the RV 112 is expelled from the heart 101 into the pulmonary artery. Blood expelled into the pulmonary artery flows into the lungs where the blood is oxygenated and thereafter flows back to the LA 110. The oxygenated blood in the LA 110 flows through the mitral valve (MV) 122 into the LV 114. Blood in the LV 114 is then expelled out of the heart 101 into the ascending aorta and from there to smaller vessels of the systemic circulation. The left and right sides of the heart 101 are separated by a wall of the heart 101, referred to as the septum 124. The LAA 106 extends off of the LA 110 and is a blind-ended structure.

FIG. 1B is a cross section of the human heart 101 after dispensing of the clip 104 by the clip applier 102. The end effector 103 of clip applier 102 is in a closed position, reducing the size of the end effector for retraction from the patient. The clip 104 closed on the LAA closes off a pocket delineated by the LAA 106 to eliminate clot formation within the pocket being distributed to the brain, thus causing a stroke. As used herein, "closed" may describe the condition of a clip in which opposed clamping portions of the clip are closer together than in an open condition, so that the clamping portions can at least partially occlude an anatomical structure located therebetween. In some embodiments, a clip may be in a closed condition when there is a gap between opposed clamping portions. That is, the opposed clamping portions need not be in contact with one another in the closed configuration. Aspects of the present disclosure provide improvements to the clip and dispenser as disclosed for example in U.S. Pat. No. 8,852,218, the disclosure of which is hereby incorporated by reference in its entirety.

FIG. 2A is a side view of the clip applier 102 having the end effector 103 in an open position as actuated by a handle 130. FIG. 2B is a side view of the clip applier 102 having the end effector 103 is in a closed position as actuated by the handle 130. With reference to FIGS. 2A-2B, clip applier 102 includes a stiff or bendable shaft 132 proximally attached to the end effector 103, which in turn is distally attached to the handle 130. A pistol grip 134 of the handle 130 is provided as a base structure for placing against a palm 136 of a hand 138 of a user 140. Upper one or more finger(s) 142a-142b may grip and actuate a crimp trigger 144 that is pivotally coupled to the handle 130. One or more fingers 142a-142d may grip and actuate an opening handle 146 that is pivotally coupled to the handle 130. A thumb finger 142e of the hand 138 may depress a deployment tab 147 pivotally extending from the handle 130 to release the clip 104 from the end effector 103.

In the illustrated embodiment, the end effector 103 of the clip dispensing device 102 includes a first channel 148, such as an upper jaw, that receives and engages a first elongate beam 150a of the clip 104. The end effector 103 of the clip dispensing device 102 includes a second channel 152, such as a lower jaw, that receives and engages a second elongate beam 150b of the clip 104. The clip 104 includes at least one strand 154, such as suture(s), that forms a loop through the first and the second elongate beams 150a-150b and extends terminal segments 156a-156b proximally through a clip setting mechanism 158. The clip applier 102 has a closure mechanism 160 coupled to the opening handle 146 that proximally draws the terminal segments 156a-156b of the at least one strand 154 to close the clip 104. The clip applier 102 has a release mechanism 162 that is coupled to the deployment tab 147 that actuates the release mechanism 162 to release the end effector 103 from the clip 104, allowing the end effector 103 to open away from the clip 104 that is in a clamped state.

In one or more embodiments, the clip setting mechanism 158 of the clip 104 includes or wholly comprises a crimping sleeve that is crimped to retain the clip 104 in a closed position by actuating a crimping tool 164 of the clip applier 102. In one or more embodiments, an exemplary method of operation 700 includes actuating the release mechanism 162 that actuates a strand cutter 166 that severs proximal terminal segments 156a-156b of the at least one strand 154 proximal to the clip setting mechanism 158.

FIG. 3A is a three-dimensional view of an example single-loop clip 104a that is in an open position. FIG. 3B is a three-dimensional view of the single-loop clip 104a that is in a closed position. In the illustrated embodiment, single-loop clip 104a includes the first elongate beam 150a that is rigid and that has a first bore 168a open at first distal end 170a and a first proximal end 171a. With reference to FIGS. 3A-3B, single-loop clip 104a includes the second elongate beam 150b that is rigid and that has a second bore 168b open at a second distal end 170b and a second proximal end 171b. An elongate strand 154a, such as a slidable suture, is positioned through the first bore 168a and the second bore 168b extending proximally respective first and second terminal segments 156a-156b from the first and the second proximal ends 171a-171b of the first and the second elongate beams 150a-150b. The clip setting mechanism 158 encompasses the first and the second terminal segments 156a-156b and is proximate to the first and the second proximal ends 171a-171b of the first and the second elongate beams 150a-150b to form a single strand loop 172a. The clip setting mechanism 158 is configured to: (i) allow cinching of the elongate strand 154a to reduce a size of the single strand loop 172a, bringing closer together the first and the second elongate beams 150a-150b; and (ii) retain the single strand loop 172a in a cinched (closed or clamped) position. In one or more embodiments, the clip setting mechanism 158 is a crimping sleeve. In one or more embodiments, the clip setting mechanism 158 is a one-way knot, such as a Meltzer knot.

FIG. 4 is a side view of the single-loop clip 104a annotated with forces ("F") and tension ("T") between arrows between Points A-E when closed around an object. Point "A" is provided by first proximal end 171a of first elongate beam 150a. Point "B" is provided by first distal end 170a of first elongate beam 150a. Point "C" is provided by second distal end 170b of second elongate beam 150b. Point "D" is provided by second proximal end 171b of second elongate beam 150b. Point "E" is provided by clip setting mechanism 158. Single strand loop 172a couples together Points A-E and is under tension to impart forces via elongate beams 150a-150b.

Thus, the present disclosure provides a clip 104a and clip applier 102 that uses two rigid beams (150a-150b) and at least one elongate strand (e.g., slidable suture) (154a) to connect the beams together and apply clamping force to the LAA. The suture (154a) can be preferably fixed in position with a crimp sleeve (158) that has minimal friction so the clip 104a can be opened and repositioned prior so crimping the sleeve. Also, when the sleeve 158 is crimped, the suture 154a is held securely. The clip setting mechanism 158 can also be a friction knot (e.g., Meltzer knot) that is balanced to slide without too much force yet enough force to securely lock the clip 104a closed so the clip 104a does not loosen. Spring clips provide a dynamic force (continuous closing force) to compensate for atrophy of the appendage over time. Spring clips have a force of approximately 2.0 lbs. at about 2 mm. Since the clip 104a according to the present disclosure does not have an elastic member, the clip 104a will close with greater force and compress the appendage to a greater extent to compensate for atrophy.

In some embodiments, as the single strand loop 172a is pulled, there are frictional losses in joints A, B, C, and D. A reasonable estimate for the coefficient of friction is about 0.3, which means the force will drop about 30% at each joint. The losses in the crimp sleeve E are not included since those forces do not impact the clip force balance. In this case, a force is applied to suture ends 156a and 156b. For example, about 5.0 lbs of tension may be generated in the suture 154a in lengths EA and ED. Frictional losses of 30% in joints A and D drops the tension in lengths AB and CD to about 3.5 lbs. Again the 30% friction loss in joints B and C drops the tension to about 2.45 lbs. This results in an unbalanced clamping force with side AD having about 5 lbs of clamping force and side BC with about half the force at about 2.45 lbs. Where the goal is to have even clamping pressure, this mismatch may not be desirable. In addition, this design may not constrain the tubes so parallel closure may be unpredictable.

FIG. 5A is a three-dimensional view of an example dual-loop clip 104b that is in an open position. FIG. 5B is a three-dimensional view of the dual-loop clip 104b that is in a closed position. In the illustrated embodiment, dual-loop clip 104b includes the first elongate beam 150a that is rigid and that has a first bore 168a open at first distal end 170a and a first proximal end 171a. With reference to FIGS. 5A-5B, dual-loop clip 104b includes the second elongate beam 150b that is rigid and that has a second bore 168b open at a second distal end 170b and a second proximal end 171b. A first elongate strand 154a, such as a slidable suture, is positioned through the first bore 168a and is distally connected to the second distal end 170b of the second elongate beam 150b. The first elongate strand 154a extends proximally at a first terminal segment 156a from the first proximal end 171a of the first elongate beam 150a. A second elongate strand 154b, such as a slidable suture, is positioned through the second bore 168b and is distally connected to the first distal end 170a of the first elongate beam 150a. The second elongate strand 154b extends proximally at a second terminal segment 156b from the second proximal end 171b of the second elongate beam 150b. The clip setting mechanism 158 encompasses the first and the second terminal segments 156a-156b and is proximate to the first and the second proximal ends 171a-171b of the first and the second elongate beams 150a-150b to form a dual-strand loop 172b. The clip setting mechanism 158 is configured to: (i) allow cinching of the elongate strands 154*a*-154*b* to reduce a size of the dual-strand loop 172*b*, bringing closer together the first and the second elongate beams 150*a*-150*b*; and (ii) retain the dual strand loop 172*b* in a cinched (closed or clamped) position. In one or more embodiments, the clip setting mechanism 158 is a crimping sleeve. In one or more embodiments, the clip setting mechanism 158 is a one-way knot, such as a Meltzer knot.

FIG. 6 is a side view of the dual-loop clip 104*b* annotated with forces ("F") and tension ("T") between arrows between Points A-E when closed around an object. Point "A" is provided by first proximal end 171*a* of first elongate beam 150*a*. Point "B" is provided by first distal end 170*a* of first elongate beam 150*a*. Point "C" is provided by second distal end 170*b* of second elongate beam 150*b*. Point "D" is provided by second proximal end 171*b* of second elongate beam 150*b*. Point "E" is provided by clip setting mechanism 158. Dual strand loop 172*b* couples together Points A-E and is under tension to impart forces via elongate beams 150*a*-150*b*.

In some embodiments, as the sutures (154*a*-154*b*) are pulled, there are frictional losses in joints A, B, C, and D. Using the same estimate for the coefficient of friction of 0.3, the calculation is similar as to FIG. 4 for the single loop clip 104*a*. Again, a force is applied to suture ends 1 and 2 (156*a*-156*b*). For example, about 5.0 lbs of tension is generated in suture 154*a*-154*b* lengths EA and ED. Frictional losses of 30% in joints A and D drops the tension in lengths AB and CD to about 3.5 lbs. Again the 30% friction loss in joints B and C drops the tension to about 2.45 lbs. Since distal portions of the sutures (154*a*-154*b*) overlap, their tensile forces are additive, doubling the resultant force on the distal end BC. This results in a more balanced clamping force with side AD having about 5 lbs of clamping force and side BC with about the same force at about 4.9 lbs. The goal is to have even clamping pressure, which this design provides. In addition, the beams are constrained better by anchoring the sutures (154*a*-154*b*) at the distal ends.

In some example embodiments according to at least some aspects of the present disclosure, at least some components of exclusion devices may be constructed from bioabsorbable and/or resorbable materials. As used herein, "bioabsorbable" may describe an object that is capable of being absorbed into living tissue, such as after surgical implantation of the object in a patient's body. As used herein, "resorbable" may refer to an object that is capable of being broken down and assimilated, such as after surgical implantation of the object in a patient's body. Bioabsorbable and/or resorbable materials utilized in various embodiments may include, for example and without limitation, metal alloys (e.g., magnesium alloys, zinc alloys, iron alloys) and/or polymers (e.g., poly(lactic acid) (PLLA), polycaprolactone (PCL)). For example, in one embodiment, structural components (e.g., springs, beams, etc.) may be constructed from a magnesium alloy, which may be at least partially enclosed within a cover constructed from PLLA. In some example embodiments, all or substantially all of the components of an exclusion device may be constructed from bioabsorbable and/or resorbable materials. That is, after sufficient time, all or substantially all of the components of some such exclusion devices may degrade so that the exclusion device and components thereof are no longer present in the patient's body. In other example embodiments, some components of an exclusion device may be constructed from bioabsorbable and/or resorbable materials and other components of the exclusion device may be constructed from materials that are not configured for bioabsorption and/or resorption. That is, at least some components of such exclusion devices may be constructed from materials configured to resist degradation after implantation so that some such components may remain within the patient's body. Generally, both degradable and non-degradable components may be constructed from biocompatible materials.

FIG. 7 is a flow diagram presenting an example method 700 for surgically closing and applying an occlusion clip on a tissue appendage of a patient using a clip applier for minimizing or eliminating the tissue appendage. Method 700 may be performed using components of like names described in the preceding FIGS. 1A-1B, 2A-2B, 3A-3B, 4, 5A-5B, and 6. With reference to FIG. 7, method 700 includes providing an occlusion clip including at least one strand that forms a loop through a first elongate beam and a second elongate beam and extends terminal segments proximally through a clip setting mechanism (block 702). Method 700 includes positioning the occlusion clip in an end effector of a clip applier (block 704). Method 700 includes receiving and engaging the first elongate beam of the occlusion clip in a first channel of the end effector (block 706). Method 700 includes receiving and engaging the second elongate beam of the occlusion clip in a second channel of the end effector that opposes the first channel (block 708). Method 700 includes inserting the end effector of the clip applier into a body cavity of a patent (block 710). Method 700 includes positioning an opening between the first and the second elongate beams of the occlusion clip around a tissue appendage of the patient (block 712), such as the left atrial appendage. Method 700 includes actuating a closure mechanism of the clip applier that proximally draws the terminal segments of the at least one strand to close the occlusion clip and closes the first and the second channel of the end effector (block 714) holding the occlusion clip beams. Method 700 includes actuating a release mechanism that actuates to release the end effector from the occlusion clip, allowing the end effector to open away from the occlusion clip in a clamped state (block 716). Method 700 includes withdrawing the end effector from the patient (block 718).

Various example methods according to at least some aspects of the present disclosure may include one or more of the operations associated with one or more of blocks 702-718 of method 700. For example, a method of constructing an occlusion device and applier may include operations similar to blocks 702-708. As another example, a method of occluding an anatomical structure may include operations similar to blocks 710-718.

In one or more embodiments, the at least one elongate strand is positioned through the first bore and the second bore extending proximally respective first and second terminal segments 156*a*-156*b* from the first and the second proximal ends of the first and the second elongate beams.

In one or more embodiments, the at least one elongate strand includes first and second elongate strands that combine to form a loop and that distally overlaps. The first elongate strand has a first distal terminal segment coupled to the second distal end of the second elongate beam and extending through the first bore of the first elongate beam from the first distal end to extend a first proximal segment proximally from the first proximal end. The second elongate strand has a second distal terminal segment coupled to the first distal end of the first elongate beam and extending through the second bore of the second elongate beam from the second distal end to extend a second proximal terminal segment proximally from the second proximal end.

In one or more embodiments, the clip setting mechanism of the occlusion clip includes or wholly comprises a crimping sleeve. Method 700 may further include actuating a crimping tool of the clip applier to crimp the crimping sleeve.

In one or more embodiments, method 700 includes actuating the release mechanism by actuating a strand cutter that severs the at least one strand proximal to the clip setting mechanism.

Unless specifically indicated, it will be understood that the description of the structure, function, and/or methodology with respect to any illustrative embodiment herein may apply to any other illustrative embodiments. More generally, it is within the scope of the present disclosure to utilize any one or more features of any one or more example embodiments described herein in connection with any other one or more features of any other one or more other example embodiments described herein. Accordingly, any combination of any of the features or embodiments described herein is within the scope of this disclosure.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope of the disclosure. Likewise, it is to be understood that it is not necessary to meet any or all of the identified advantages or objects disclosed herein in order to fall within the scope of the disclosure, since inherent and/or unforeseen advantages may exist even though they may not have been explicitly discussed herein.

While the innovation has been described with reference to exemplary embodiments, it will be understood by those skilled in the art that various changes may be made, and equivalents may be substituted for elements thereof without departing from the scope of the innovation. In addition, many modifications may be made to adapt a particular system, device, or component thereof to the teachings of the innovation without departing from the essential scope thereof. Therefore, it is intended that the innovation not be limited to the particular embodiments disclosed for carrying out this innovation, but that the innovation will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the innovation. As used herein, the singular forms "a", "an" and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present innovation has been presented for purposes of illustration and description but is not intended to be exhaustive or limited to the innovation in the form disclosed. Many modifications and variations will be apparent to those of ordinary skill in the art without departing from the scope and spirit of the innovation. The embodiments were chosen and described in order to best explain the principles of the innovation and the practical application, and to enable others of ordinary skill in the art to understand the innovation for various embodiments with various modifications as are suited to the particular use contemplated.

What is claimed is:

1. An occlusion clip for an anatomical structure, the occlusion clip comprising:
   a first elongate rigid beam comprising a first bore open at first distal end and a first proximal end;
   a second elongate rigid beam comprising a second bore open at second distal end and a second proximal end;
   an elongate strand of suture that is positioned to slide through the first bore and the second bore extending proximally at respective first and second terminal segments from the first and the second proximal ends of the first and the second elongate rigid beams; and
   a clip setting mechanism that encompasses the first terminal segment and the second terminal segment of the elongate strand of suture and that is proximate to the first and the second proximal ends of the first and the second elongate rigid beams, the clip setting mechanism configured to: (i) allow cinching of the elongate strand of suture to reduce a size of the single strand loop, bringing closer together the first and the second elongate rigid beams; and (ii) retain the single strand loop in a cinched position.

2. The apparatus of claim 1, wherein the clip setting mechanism comprises a crimping sleeve.

3. The apparatus of claim 1, wherein the clip setting mechanism comprises a one-way knot.

4. The apparatus of claim 3, wherein the one-way knot is a Meltzer knot.

5. An occlusion clip for an anatomical structure, the occlusion clip comprising:
   a first elongate beam comprising a first bore open at first distal end and a first proximal end;
   a second elongate beam comprising a second bore open at second distal end and a second proximal end;
   first and second elongate strands that combine to form a loop and that distally overlap, wherein:
      the first elongate strand has a first distal terminal segment coupled to the second distal end of the second elongate beam and extending through the first bore of the first elongate beam from the first distal end to extend a first proximal segment proximally from the first proximal end; and
      the second elongate strand has a second distal terminal segment coupled to the first distal end of the first elongate beam and extending through the second bore of the second elongate beam from the second distal end to extend a second proximal terminal segment proximally from the second proximal end; and
   a clip setting mechanism that encompasses the first and the second terminal segments respectively of the first and the second elongate strands and that is proximate to the first and the second proximal ends of the first and the second elongate beams, the clip setting mechanism configured to: (i) allow cinching of the elongate strand to reduce a size of the single strand loop, bringing together the first and the second elongate beams; and (ii) retain the single strand loop in a cinched position.

6. The apparatus of claim 5, wherein the clip setting mechanism comprises a crimping sleeve.

7. The apparatus of claim 5, wherein the clip setting mechanism comprises a one-way knot.

8. The apparatus of claim 7, wherein the one-way knot is a Meltzer knot.

9. A clip dispensing device, comprising:

an end effector comprising: (i) a first channel that receives and engages a first elongate beam of an occlusion clip; and (ii) a second channel that receives and engages a second elongate beam of the occlusion clip, the occlusion clip comprising at least one strand that forms a loop through the first and the second elongate beams and extends terminal segments proximally through a clip setting mechanism;

a closure mechanism operative to proximally draw the terminal segments of the at least one strand to close the occlusion clip;

a release mechanism that actuates to release the end effector from the occlusion clip, allowing the end effector to open away from the occlusion clip in a clamped state.

10. The clip dispensing device of claim 9, wherein the clip setting mechanism of the occlusion clip comprises a crimping sleeve, the clip dispensing device comprising a crimping tool positioned to contact the crimping sleeve and configured for actuation to crimp the crimping sleeve.

11. The clip dispensing device of claim 9, wherein the release mechanism comprises a strand cutter operative to severs the at least one strand proximal to the clip setting mechanism.

12. A method comprising:

surgically inserting an end effector of a clip applier into a body cavity of a patent, the end effector comprising: (i) a first channel that receives and engages a first elongate beam of an occlusion clip; and (ii) a second channel that receives and engages a second elongate beam of the occlusion clip, the occlusion clip comprising at least one strand that forms a loop through the first and the second elongate beams and extends terminal segments proximally through a clip setting mechanism;

positioning an opening between the first and the second elongate beams of the occlusion clip around a tissue appendage of the patient;

actuating a closure mechanism that proximally draws the terminal segments of the at least one strand to close the occlusion clip and close the first and the second channel of the end effector; and actuating a release mechanism to release the end effector from the occlusion clip, allowing the end effector to open away from the occlusion clip in a clamped state.

13. The method of claim 12, wherein the at least one elongate strand is positioned through the first bore and the second bore extending proximally at respective first and second terminal segments from the first and the second proximal ends of the first and the second elongate beams.

14. The method of claim 12, wherein the at least one elongate strand comprises first and second elongate strands that combine to form a loop and that distally overlap, wherein:

the first elongate strand has a first distal terminal segment coupled to the second distal end of the second elongate beam and extending through the first bore of the first elongate beam from the first distal end to extend a first proximal segment proximally from the first proximal end; and the second elongate strand has a second distal terminal segment coupled to the first distal end of the first elongate beam and extending through the second bore of the second elongate beam from the second distal end to extend a second proximal terminal segment proximally from the second proximal end.

15. The method of claim 12, wherein the clip setting mechanism of the occlusion clip comprises a crimping sleeve, the method further comprising actuating a crimping tool of the clip applier to crimp the crimping sleeve.

16. The method of claim 12, wherein actuating the release mechanism comprises actuating a strand cutter that severs the at least one strand proximal to the clip setting mechanism.

* * * * *